(12) United States Patent
Lintz et al.

(10) Patent No.: US 10,699,143 B2
(45) Date of Patent: Jun. 30, 2020

(54) SYSTEM AND METHOD FOR VEHICLE OCCUPANT IDENTIFICATION AND MONITORING

(71) Applicant: GENTEX CORPORATION, Zeeland, MI (US)

(72) Inventors: Joshua D. Lintz, Allendale, MI (US); Andrew D. Weller, Holland, MI (US)

(73) Assignee: GENTEX CORPORATION, Zeeland, MI (US)

( * ) Notice: Subject to any disclaimer, the term of this patent is extended or adjusted under 35 U.S.C. 154(b) by 90 days.

(21) Appl. No.: 15/915,375

(22) Filed: Mar. 8, 2018

(65) Prior Publication Data

US 2018/0260640 A1 Sep. 13, 2018

Related U.S. Application Data

(60) Provisional application No. 62/469,719, filed on Mar. 10, 2017.

(51) Int. Cl.
*G06K 9/00* (2006.01)
*G06K 9/20* (2006.01)
(Continued)

(52) U.S. Cl.
CPC ............ *G06K 9/00832* (2013.01); *A61B 5/18* (2013.01); *B60K 28/02* (2013.01); *B60Q 3/00* (2013.01);
(Continued)

(58) Field of Classification Search
CPC ........... G06K 9/00832; G06K 9/00838; G06K 9/00845; B60R 25/25; B60R 25/255;
(Continued)

(56) References Cited

U.S. PATENT DOCUMENTS 5,570,698 A * 11/1996 Liang ................ A61B 5/18 600/558
5,729,619 A * 3/1998 Puma .................. B60K 28/063 382/115

(Continued)

FOREIGN PATENT DOCUMENTS

EP 1452127 A1 9/2004
WO WO-0208022 A2 * 1/2002 ............ B60R 25/25
(Continued)

OTHER PUBLICATIONS

International Search Report dated Aug. 23, 2018, in correspondence to PCT application No. PCT/US 2018/021480, 8 pages.
(Continued)

*Primary Examiner* — David N Werner
(74) *Attorney, Agent, or Firm* — Price Heneveld LLP; Bradley D. Johnson

(57) ABSTRACT

An imaging system and method are provided herein. A first light source is configured to project a first illumination onto a vehicle occupant. A second light source is configured to project a second illumination onto the vehicle occupant. An imager is configured to acquire one or more images of a biometric feature of the vehicle occupant and generate image data corresponding to the one or more acquired images. The imager is further configured with a variable field of view based on which of the first and second light sources is activated.

19 Claims, 4 Drawing Sheets

(51) Int. Cl.
*B60R 1/12* (2006.01)
*B60R 1/04* (2006.01)
*H04N 5/232* (2006.01)
*H04N 5/235* (2006.01)
*H04N 5/225* (2006.01)
*A61B 5/18* (2006.01)
*G08B 21/06* (2006.01)
*B60K 28/02* (2006.01)
*B60Q 3/00* (2017.01)
*G02F 1/153* (2006.01)
*G02F 1/1514* (2019.01)

(52) U.S. Cl.
CPC .......... *B60R 1/04* (2013.01); *B60R 1/12* (2013.01); *G06K 9/00248* (2013.01); *G06K 9/00255* (2013.01); *G06K 9/00604* (2013.01); *G06K 9/00838* (2013.01); *G06K 9/00845* (2013.01); *G06K 9/2018* (2013.01); *G06K 9/2027* (2013.01); *G08B 21/06* (2013.01); *H04N 5/2256* (2013.01); *H04N 5/2354* (2013.01); *H04N 5/23296* (2013.01); *B60R 2001/1253* (2013.01); *B60R 2300/103* (2013.01); *G02F 1/153* (2013.01); *G02F 2001/15145* (2019.01)

(58) Field of Classification Search
CPC ..... B60R 2300/103; G08B 21/06; A61B 5/18; B60K 28/02; B60Q 3/00
See application file for complete search history.

(56) References Cited

U.S. PATENT DOCUMENTS

| | | | | |
|---|---|---|---|---|
| 6,714,665 | B1 | 3/2004 | Hanna et al. | |
| 7,202,793 | B2* | 4/2007 | Grace | A61B 5/1103 340/576 |
| 7,570,785 | B2* | 8/2009 | Breed | B60K 28/066 382/100 |
| 2004/0151344 | A1* | 8/2004 | Farmer | G06K 9/00362 382/103 |
| 2005/0102080 | A1* | 5/2005 | Dell' Eva | G06K 9/00362 701/45 |
| 2005/0111700 | A1* | 5/2005 | O'Boyle | G06K 9/00201 382/104 |
| 2008/0288143 | A1* | 11/2008 | Smith | A61B 5/18 701/49 |
| 2015/0363986 | A1 | 12/2015 | Hoyos et al. | |
| 2017/0046582 | A1* | 2/2017 | Hoshiya | G03B 15/00 |
| 2017/0210357 | A1* | 7/2017 | Nagai | B60K 28/06 |
| 2017/0264797 | A1* | 9/2017 | Trinh | B60K 35/00 |
| 2018/0005057 | A1* | 1/2018 | Lee | B60R 1/00 |
| 2018/0016579 | A1* | 1/2018 | Rozet | C12N 15/1137 |
| 2018/0178729 | A1* | 6/2018 | Festerling, Jr. | G06K 9/00832 |
| 2018/0229725 | A1* | 8/2018 | Akama | B60W 40/00 |

FOREIGN PATENT DOCUMENTS

WO 20040341832 A2 3/2007
WO 20160201058 A1 12/2016

OTHER PUBLICATIONS

Ebisawa Y et al: "Effectiveness of pupil area detection technique using two light sources and image difference method", Engineering in Medicine and Biology Society, 1993. Proceedings of the 15th Annual International Conference of the IEEE Oct. 28-31, 1993, Piscataway, NJ, USA, IEEE, Oct. 28, 1993, pp. 1268-1269, XP010574813, ISBN: 978-0-7803-1377-4.

Extended European Search Report dated Feb. 4, 2020, in corresponding European application No. 18763778, 12 pages.

* cited by examiner

SYSTEM AND METHOD FOR VEHICLE OCCUPANT IDENTIFICATION AND MONITORING

CROSS-REFERENCE TO RELATED APPLICATION

This application claims the benefit of and priority to U.S. Provisional Patent Application No. 62/469,719, filed on Mar. 10, 2017, entitled IMAGING SYSTEM AND METHOD FOR VEHICLE OCCUPANT IDENTIFICATION AND MONITORING, the entire disclosure of which is hereby incorporated herein by reference.

FIELD OF THE INVENTION

The present invention generally relates to an imaging system and method of a vehicle, and more particularly, to an imaging system and method for driver identification and monitoring.

SUMMARY OF THE INVENTION

According to one aspect of the present invention, an imaging system is provided. A first light source is configured to project a first illumination onto a vehicle occupant. A second light source is configured to project a second illumination onto the vehicle occupant. An imager is configured to acquire one or more images of a biometric feature of the vehicle occupant and generate image data corresponding to the one or more acquired images. The imager is further configured with a variable field of view based on which of the first and second light sources is activated. The first and second illuminations may comprise light in a near infrared spectrum. The first and second illuminations may have the same wavelength, or the first and second illuminations may have different wavelengths, with the second illumination having a longer wavelength than the first illumination.

According to another aspect of the present invention, an imaging system is provided. A first light source is configured to project a first illumination onto a vehicle occupant. A second light source is configured to project a second illumination onto the vehicle occupant. An imager has a variable field of view and is configured to acquire one or more images of a biometric feature of the vehicle occupant and generate image data corresponding to the one or more acquired images. A controller is configured to execute a first identification function by activating only the first light source and processing image data generated by the imager while operating with a first field of view. The controller is also configured to execute a second identification function by activating only the second light source and processing image data generated by the imager while operating with a second field of view.

According to yet another aspect of the present invention, an imaging method is provided and includes the steps of projecting a first illumination or a second illumination onto a vehicle occupant; providing an imager having a variable field of view based on which of the first and second illumination is being projected; using the imager to acquire one or more images of a biometric feature of the vehicle occupant; identifying the vehicle occupant by projecting only the first illumination and processing image data generated while the imager is operating with a narrow field of view; and monitoring the vehicle occupant by projecting only the second illumination and processing image data generated while the imager is operating with a wide field of view. In some embodiments, when identifying the vehicle occupant, the biometric feature may comprise an iris of the vehicle occupant. In some embodiments, when monitoring the vehicle occupant, the biometric feature may comprise at least one of a face and a body of the vehicle occupant.

These and other aspects, objects, and features of the present invention will be understood and appreciated by those skilled in the art upon studying the following specification, claims, and appended drawings.

DETAILED DESCRIPTION OF THE PREFERRED EMBODIMENTS

As required, detailed embodiments of the present invention are disclosed herein.

However, it is to be understood that the disclosed embodiments are merely exemplary of the invention that may be embodied in various and alternative forms. The figures are not necessarily to a detailed design and some schematics may be exaggerated or minimized to show function overview. Therefore, specific structural and functional details disclosed herein are not to be interpreted as limiting, but merely as a representative basis for teaching one skilled in the art to variously employ the present invention.

Figure 1:
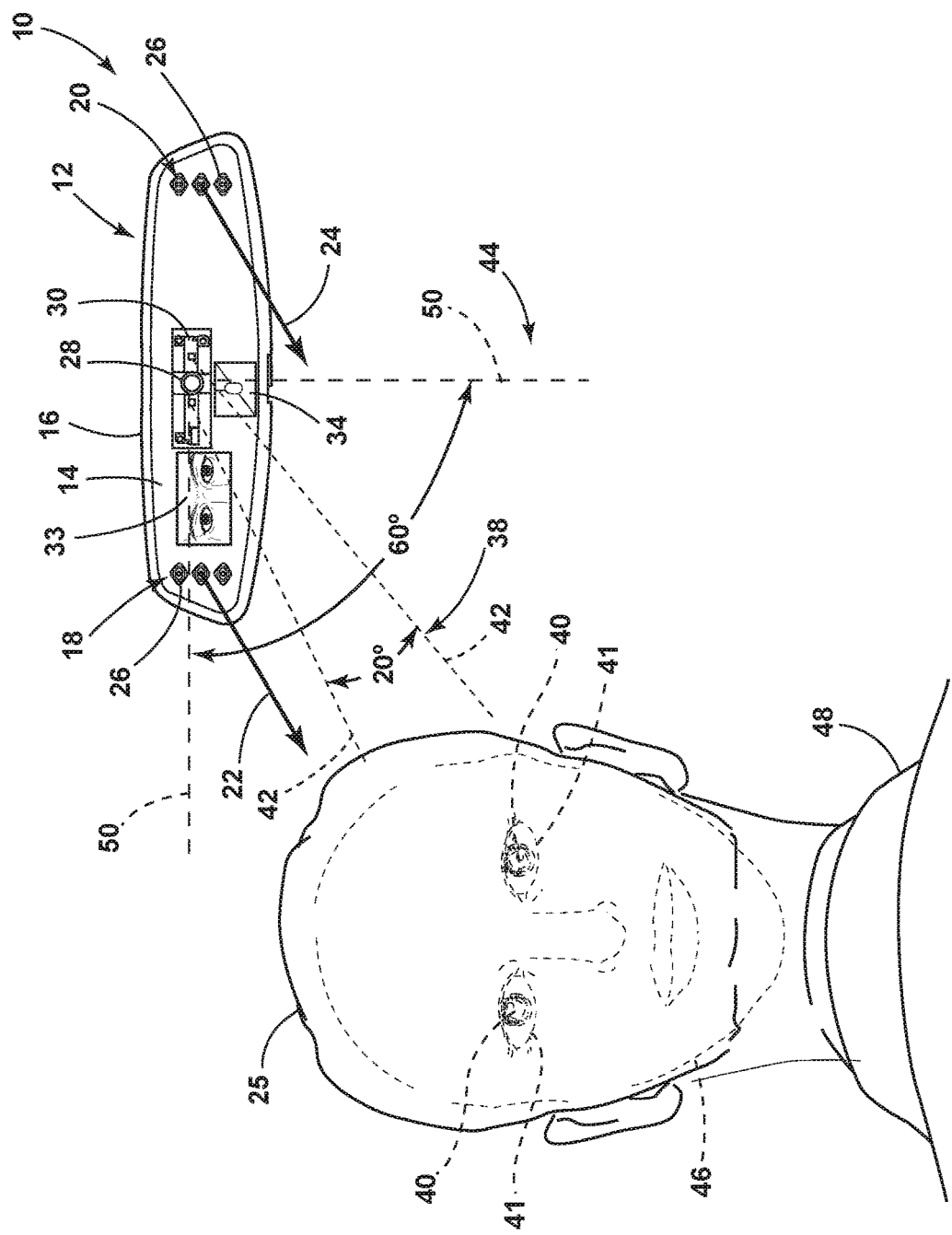
FIG. 1 is a perspective view of an imaging system incorporated in an interior rearview mirror assembly.

For purposes of description herein, the terms "upper," "lower," "right," "left," "rear," "front," "vertical," "horizontal," and derivatives thereof shall relate to the invention as oriented in FIG. 1. Unless stated otherwise, the term "front" shall refer to the surface of the element closer to an intended viewer of the mirror element, and the term "rear" shall refer to the surface of the element further from the intended viewer of the mirror element. However, it is to be understood that the invention may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

The terms "including," "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises a . . . " does not, without more constraints, preclude the existence of additional identical elements in the process, method, article, or apparatus that comprises the element.

As used herein, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

Figure 2:
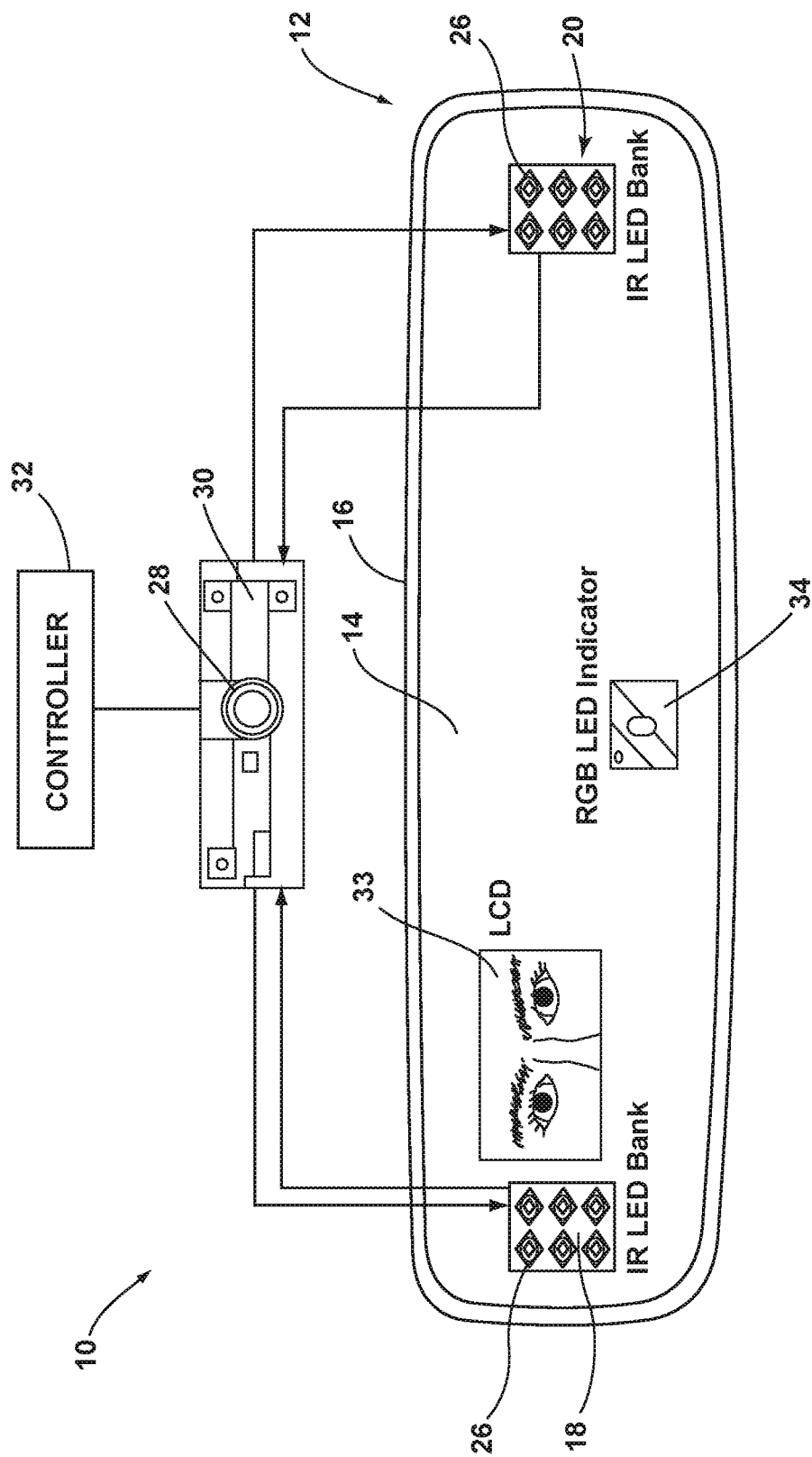
FIG. 2 is a schematic view of the interior rearview mirror assembly shown in FIG. 1.

Referring to FIGS. 1 and 2, reference numeral 10 generally designates an imaging system operable to perform one or more identification functions. In the present embodiment, the imaging system 10 is exemplarily shown incorporated into an interior rearview mirror assembly 12 of an automotive vehicle. The interior rearview mirror assembly 12 may be configured as an electro-optic rearview mirror assembly that is partially reflective and partially transmissive and having a mirror element 14 coupled to a housing 16.

A first light source 18 and a second light source 20 are disposed inside the housing 16 and located behind the mirror element 14. While the first and second light sources 18, 20 are shown located at opposite sides of the housing 16, it is to be understood that their illustrated positions should not be construed as limiting. In alternative embodiments, the first and/or second light sources 18, 20 may be located elsewhere in the housing 16 or otherwise be provided on external portions of the housing 16.

As shown in FIG. 1, the first light source 18 is configured to project a first illumination generally represented by arrow 22 and the second light source 20 is configured to project a second illumination generally represented by arrow 24. The first and second illuminations are projected through the mirror element 14 onto a vehicle occupant such as driver 25. In some embodiments, the first and second illumination use the same wavelength. In some embodiments, the first illumination and the second illumination each include a distinct wavelength selected from a near infrared (NIR) spectrum including wavelengths ranging from 800 nm to 950 nm. The second illumination may have a longer wavelength than the first illumination. In some embodiments, the first illumination may have a wavelength of about 810 nm and the second illumination may have a wavelength of about 940 nm. In some embodiments, the first illumination may have a wavelength of about 860 nm and the second illumination may have a wavelength of about 940 nm. In some embodiments, the first illumination may have a wavelength of about 880 and the second illumination may have a wavelength of 940 nm. The wavelengths of the first and second illuminations are only provided as examples and are not intended to be limiting.

It is generally contemplated that the first and second light sources 18, 20 may each include one or more infrared emitter banks 26 that emit the first and second illumination, respectively. Each emitter bank 26 may include a plurality of light emitting diodes (LEDs), which may be grouped in a matrix or otherwise grouped in other arrangements. It will be understood that the emitter banks 26 may be positioned anywhere inside the housing 16 that would enable the first and second illumination to be projected onto the driver 25.

As shown in FIGS. 1 and 2, an imager 28 is disposed inside the housing 16 and is exemplarily shown located in a generally central location behind the mirror element 14. The imager 28 is configured to acquire one or more images of a biometric feature of the driver 25 and generate image data corresponding to the one or more acquired images. The imager 28 is further configured with a variable field of view based on which of the first and second light sources 18, 20 is activated.

The first light source 18, the second light source 20, and the imager 28 may be electrically coupled to a printed circuit board (PCB) 30 and are in communication with a controller 32. The controller 32 may be located on the PCB 30, elsewhere located in the housing 16, or elsewhere located in the vehicle. The controller 32 may further be in communication with various devices incorporated in the interior rearview mirror assembly 12 and/or equipment of the vehicle. The controller 32 may include one or more processors configured to selectively activate the first and second light sources 18, 20, and process image data received from the imager 28 to determine an identity of the driver 25 or monitor the driver 25, among other things.

In the present embodiment, the controller 32 may communicate with a display 33 disposed inside the housing 16 of the interior rearview mirror assembly 12 and visible through the mirror element 14. The controller 32 may be configured to operate the display 33 to show image data received from the imager 28. The display 33 may be configured as a LCD, LED, OLED, plasma, DLP, or other display type. Examples of displays that may be utilized are disclosed in U.S. Pat. No. 6,572,233, entitled "Rearview Display Mirror," 8,237,909, entitled "Vehicular Rearview Mirror Assembly including Integrated Backlighting for a Liquid Crystal Display (LCD)," U.S. Pat. No. 8,411,245, entitled "Multi-Display Mirror System and Method for Expanded View around a Vehicle," and U.S. Pat. No. 8,339,526, entitled "Vehicle Rearview Mirror Assembly Including a High Intensity Display," all of which are incorporated herein by reference in their entirety.

The controller 32 may also communicate with an indicator 34 configured to output a visual notification indicating an operation state of the imaging system 10. The indicator 34 may be configured as an LED or other light source and is operable by the controller 32 to flash and/or change colors to indicate the operation state of the imaging system 10. In one specific embodiment, the indicator 34 may be configured as an RGB LED operable to indicate the operation state by emitting light expressed in a red color, a green color, a blue color, or any color combination thereof.

In the depicted embodiment of FIGS. 1 and 2, each of the first and second light sources 18, 20 is uniquely associated with an identification function executed by the controller 32. According to a first identification function, or an iris scanning function to identify a vehicle occupant (e.g., driver 25), the controller 32 activates only the first light source 18 to project the first illumination toward the driver 25. As discussed herein, the first illumination may be a NIR illumination having a wavelength in the range of about 810 nm to 880 nm. For example, the first illumination may have a wavelength of 810 nm, of 860 nm, or of 880 nm. In some embodiments, when activating only the first light source 18, the controller 32 also may operate the imager 28 with a first field of view 38 to enable image acquisition of an iris 40 of one or both eyes 41 of the driver 25. The controller 32 may process image data generated by the imager 28 while operating with the first field of view 38 to identify the driver 25. The first field of view 38 is typically a narrow field of view. In some embodiments, the first field of view 38 may have a first horizontal field component 42 of approximately 20 degrees and a similar or different vertical component (not shown). As shown in FIGS. 1 and 2, image data generated by the imager 28 may be shown on the display 33. Using the display 33 as reference, the driver 25 may adjust the position of the interior rearview mirror assembly 12 such that the image appearing on the display 33 is properly trained on the necessary biometric feature (e.g., iris 40) required to identify the driver 25. Driver identification may be used alongside vehicle security features and to authorize financial transactions.

According to a second identification function, or a driver monitoring function that includes facial recognition, the controller 32 activates only the second light source 20 to project the second illumination onto the driver 25. As discussed herein, the second illumination may be a NIR illumination having a wavelength of 940 nm. In some embodiments, when activating only the second light source 20, the controller 32 also may operate the imager 28 with a second field of view 44 to enable image acquisition of a face 46 and/or body 48 of the driver 25. The controller 32 may process image data generated by the imager 28 while operating with the second field of view 44 to monitor the driver 25. The second field of view 44 is typically a wide field of view. In some embodiments, the second field of view 44 may have a second horizontal field component 50 of approximately 60 degrees and a similar or different vertical component (not shown). As described herein, image data generated by the imager 28 may be shown on the display 33 and the driver 25 may adjust the position of the interior rearview mirror assembly 12 such that the image appearing on the display 33 is properly trained on the necessary biometric feature (e.g., face 46 and/or body 48) required to monitor the driver 25. Driver monitoring may include monitoring for sleepiness, inattentiveness, and other driver states.

According to one embodiment, it is contemplated that the controller 32 may use output (e.g., an auto gain threshold) from the imager 28 to determine characteristics (e.g., wavelength, intensity, etc.) of the first and/or the second illumination based on current vehicle and/or ambient lighting conditions. In embodiments where the interior rearview mirror assembly 12 is configured as an electro-optic rearview mirror assembly, the controller 32 may additionally or alternatively use available feedback mechanisms from a dimming controller to determine the characteristics of the first and/or the second illumination. Additionally or alternatively, the imaging system 10 may be configured to include manual entry criteria such as eye color and skin color to aid the controller 32 in determining the characteristics of the first and/or the second illumination. The criteria may be entered using any available user-input device of the vehicle. By employing one or more of the foregoing features, the imaging system 10 may benefit from improved speed and accuracy with respect to biometric capture and/or user authentication.

Figure 3:
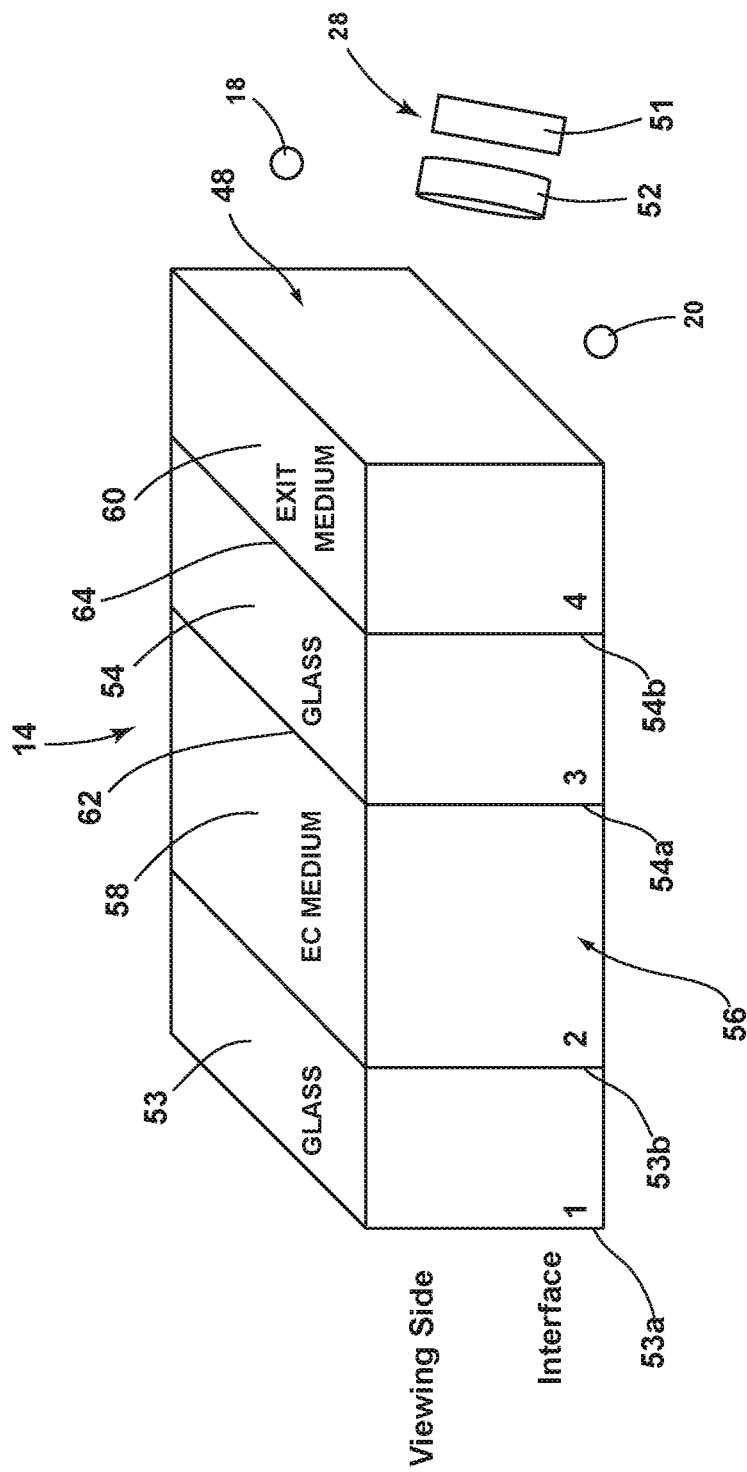
FIG. 3 illustrates an orientation between certain components of the imaging system shown in FIG. 1 with respect to a vantage point of a vehicle occupant.

Referring to FIG. 3, an orientation between the first and second light sources 18, 20, the imager 28, and the mirror element 14 is shown. For purposes of clarity, the housing 16 of the interior rearview mirror assembly 12 has been omitted. In the depicted embodiment, the mirror element 14 is disposed proximate a viewing side, or in other words, toward the front of the interior rearview mirror assembly 12 with respect to the vantage point of a vehicle occupant such as driver 25. The first and second light sources 18, 20 and the imager 28 are disposed behind mirror element 14 toward the rear of the rearview mirror assembly 12. The imager 28 includes an image sensor 51 and a lens 52 in optical communication with image sensor 51. In some embodiments, lens 52 may be operable between a plurality of fields of view including first field of view 38 and second field of view 44. In some embodiments, image sensor 51 may be without a color filter array. In some embodiments, a red clear clear clear color filter configuration may be used. In some embodiments, lens 52 may be a variable zoom lens. In some embodiments, image sensor 51 may comprise a color filter array and lens 52 may be a variable zoom lens. In some embodiments, image sensor may be without a color filter array and lens 52 may be a fixed zoom lens. The image sensor 51 may be configured as a digital charge-coupled device (CCD) or a complementary metal-oxide-semiconductor (CMOS), for example. With respect to the depicted embodiment, the contents of the housing 16 including the first and second light sources 18, 20 and the imager 28 may be concealed from view such that the interior rearview mirror assembly 12 maintains an appearance of a conventional rearview mirror.

As shown, the mirror element 14 includes a first substrate 53 (e.g., glass) having a first surface 53a corresponding to a first interface 1 and a second a surface 53b corresponding to a second interface 2. The mirror element 14 also includes a second substrate 54 (e.g., glass) having a third surface 54a corresponding to a third interface 3 and a fourth surface 54b corresponding to a fourth interface 4. The first and second substrates 53, 54 define a cavity 56 and may be disposed in parallel with each other. The cavity 56 may be completely or partially filled with an electro-optic medium 58 that may be configured as an electrochromic (EC) medium. The mirror element 14 may also include an exit medium 60 that is coupled to the fourth surface 54b of the second substrate 54.

It is contemplated that the mirror element 14 may be in communication with a dimming controller via electrical contacts and may include various seals to retain the electro-optic medium 58 between the first and second substrates 53, 54. In this configuration, the mirror element 14 may correspond to an EC mirror element configured to vary in reflectivity in response to a control signal received from the dimming controller via the electrical contacts. The control signal may change an electrical potential supplied to the mirror element 14 to control the reflectivity.

In the depicted embodiment, a transflective coating 62 is disposed on the third interface 3. The transflective coating 62 may include a layer containing silver along with additional layers such as metal, dielectric, and/or transparent conducting oxides located above or below the silver containing layer. When configured with the transflective coating 62, the mirror element 14 may generally have a nominal reflectance of 65% and a nominal transmittance of 22% in the visible range. The visible reflectance and transmittance may vary depending on design considerations and design objectives. The transmittance in the NIR spectrum may be less than the transmittance in the visible spectrum. In one embodiment, the transmittance in the NIR spectrum may be less than 20%. The relatively low transmittance in the NIR spectrum may be due to the thickness and optical constants of materials forming the transflective coating 62.

In embodiments where the first and second light sources 18, 20 are positioned behind the mirror element 14, light emitted therefrom passes through the mirror element 14 toward the viewing side and onto the driver 25. Additionally, light reflected from the driver 25 on the viewing side is transmitted back through the mirror element 14 and is received by the image sensor 51 of the imager 28. Accordingly, some embodiments of the transflective coating 62 may inhibit the first and second light sources 18, 20 and reduce their outputted light intensity. Additionally, the transflective coating 62 may inhibit light reflected from the driver 25 from being captured by the imager 28. Thus, in some embodiments, the first and second light sources 18, 20 may be configured to emit light in the NIR spectrum at a higher intensity. Furthermore, the inside rearview mirror assembly 12 may be configured to maintain a neutral color with respect to the light emitted by the first and second light sources 18, 20 and the light reflected by the driver 25.

Figure 4:
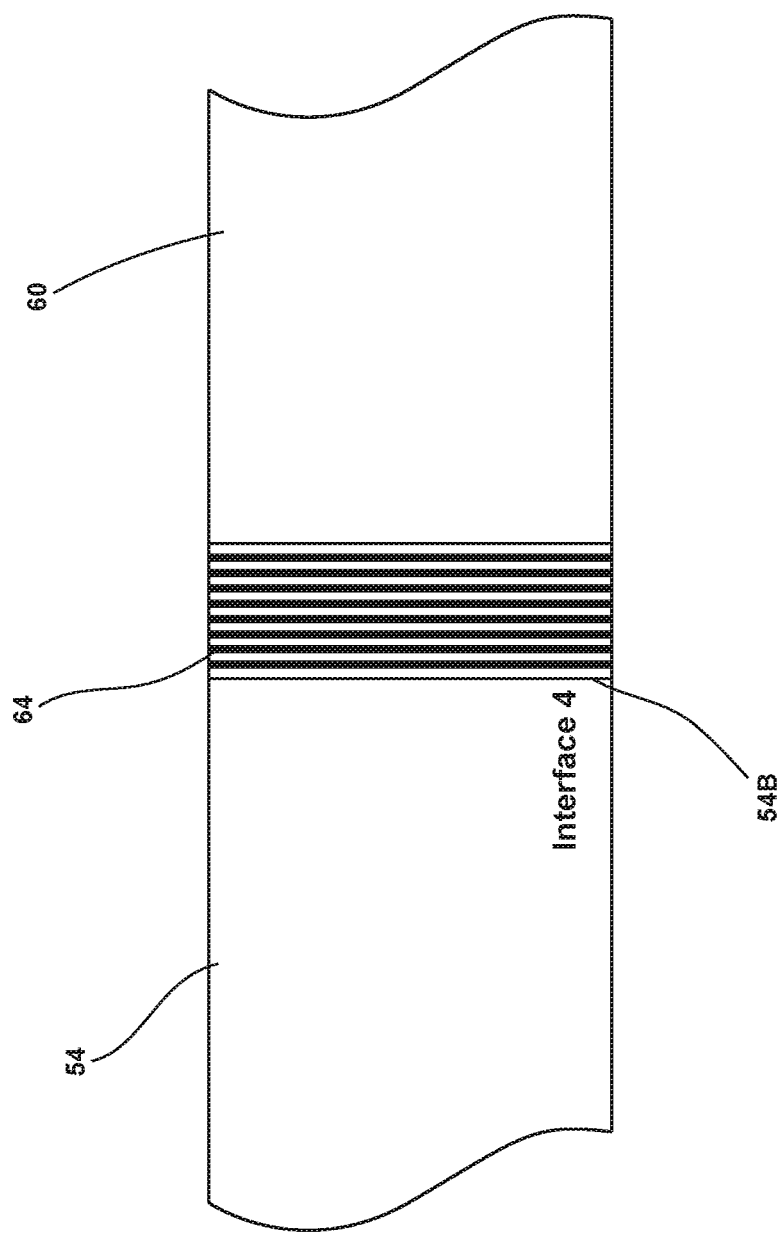
FIG. 4 illustrates a transflective coating incorporated into a mirror element of the interior rearview mirror assembly shown in FIG. 1.

Referring to FIGS. 3 and 4, the transflective coating may be implemented as a transflective dielectric coating 64 that is applied to the fourth interface 4. The transflective dielectric coating 64 would be used instead of the transflective coating 62 described herein. The transflective dielectric coating 64 is designed to resolve the issues related to the limited transmission in the NIR spectrum for the interior rearview mirror assembly 12 and provide NIR transmittance greater than about 20%. The transflective dielectric coating 64 is designed to attain a reflectance level comparable to industry standard, i.e., about 40% to 85%, or about 50% to 75%, or about 55% to 70%. Additionally, the transflective dielectric coating 64 can be designed to attain a neutral color appearance in the visible color spectrum for normal incidence viewing angle up to broad viewing angles. In this way, the disclosure provides for improved transmittance in the NIR spectrum while maintaining visible color performance.

The transflective dielectric coating 64 may include low-loss dielectric materials configured in an alternating high and low refractive index multi-layer stack. Examples of low-loss dielectric materials include, but are not limited to, niobium oxide, silicon oxide, tantalum oxide, aluminum oxide, etc. Additionally, with the tuning flexibility in an alternating high refractive index (H) and low refractive index (L) material multilayer (HL-Stack) construction, the transmittance of the transflective dielectric coating 64 in the NIR spectrum can be above 30%. In some embodiments, the NIR transmittance of the transflective dielectric coating 64 may be greater than 50%. In an exemplary embodiment, the NIR transmittance of the transflective dielectric coating 64 may be greater than 70%. In other embodiments, the NIR transmittance, for at least some wavelengths between about 800 and 940 nm, is greater than the visible transmittance by a factor of 1.5 or 2, for example.

The high refractive index (H) material may be Niobium Oxide and the low refractive index (L) material may be Silicon Dioxide. It should be understood that these two examples are not meant to be limiting. Alternate dielectric coatings may have a quantity of layers between 3 and 14 or more than 14 layers. The number of layers needed to achieve the design goals will vary with the selection of the high and low refractive index materials. Fewer layers may be needed as the difference in refractive index between the two materials increases. Conversely, more layers may be needed if the refractive index difference is less. The refractive index difference may be greater than about 0.4, greater than about 0.6, or greater than about 0.8. Additional materials may be added which have refractive indices different than the high and low refractive index materials.

Additional information on the construction of the mirror element 14 and transflective coatings can be found in U.S. patent application Ser. No. 15/372,875 to Weller et al., filed Dec. 8, 2016, and entitled "MIRROR ASSEMBLY INCORPORATING A SCANNING APPARATUS," and U.S. patent application Ser. No. 15/372,717 to Holland et al., filed Dec. 8, 2016, and entitled "IR TRANSMITTING COATING FOR ELECTRO-OPTIC ELEMENT," which are herein incorporated by reference in their entirety.

In some embodiments, the mirror element 14 may be an electrochromic element or an element such as a prism. One non-limiting example of an electro-chromic element is an electrochromic medium, which includes at least one solvent, at least one anodic material, and at least one cathodic material. Typically, both of the anodic and cathodic materials are electroactive and at least one of them is electrochromic. It will be understood that regardless of its ordinary meaning, the term "electroactive" will be defined herein as a material that undergoes a modification in its oxidation state upon exposure to a particular electrical potential difference. Additionally, it will be understood that the term "electrochromic" will be defined herein, regardless of its ordinary meaning, as a material that exhibits a change in its extinction coefficient at one or more wavelengths upon exposure to a particular electrical potential difference. Electrochromic components, as described herein, include materials whose color or opacity are affected by electric current, such that when an electrical current is applied to the material, the color or opacity change from a first phase to a second phase. The electrochromic component may be a single-layer, single-phase component, multi-layer component, or multi-phase component, as described in U.S. Pat. No. 5,928,572 entitled "Electrochromic Layer And Devices Comprising Same," U.S. Pat. No. 5,998,617 entitled "Electrochromic Compounds," U.S. Pat. No. 6,020,987 entitled "Electrochromic Medium Capable Of Producing A Pre-selected Color," U.S. Pat. No. 6,037,471 entitled "Electrochromic Compounds," U.S. Pat. No. 6,141,137 entitled "Electrochromic Media For Producing A Pre-selected Color," U.S. Pat. No. 6,241,916 entitled "Electrochromic System," U.S. Pat. No. 6,193,912 entitled "Near Infrared-Absorbing Electrochromic Compounds And Devices Comprising Same," U.S. Pat. No. 6,249,369 entitled "Coupled Electrochromic Compounds With Photostable Dication Oxidation States," and U.S. Pat. No. 6,137,620 entitled "Electrochromic Media With Concentration Enhanced Stability, Process For The Preparation Thereof and Use In Electrochromic Devices"; U.S. Pat. No. 6,519,072, entitled "Electrochromic Device"; and International Patent Application Serial Nos. PCT/US98/05570 entitled "Electrochromic Polymeric Solid Films, Manufacturing Electrochromic Devices Using Such Solid Films, And Processes For Making Such Solid Films And Devices," PCT/EP98/03862 entitled "Electrochromic Polymer System," and PCT/US98/05570 entitled "Electrochromic Polymeric Solid Films, Manufacturing Electrochromic Devices Using Such Solid Films, And Processes For Making Such Solid Films And Devices," which are herein incorporated by reference in their entirety.

The present disclosure may be used with a mounting system such as that described in U.S. Pat. Nos. 8,814,373; 8,201,800; and 8,210,695; U.S. Patent Application Publication Nos. 2014/0063630; 2013/0062497; and 2012/0327234; and U.S. Provisional Patent Application Nos. 61/709,716; 61/707,676; and 61/704,869, which are hereby incorporated herein by reference in their entirety. Further, the present disclosure may be used with a rearview packaging assembly such as that described in U.S. Pat. Nos. 8,814,373; 8,646,924; 8,643,931; and 8,264,761; U.S. Patent Application No. 2013/0194650; and U.S. Provisional Patent Application Nos. 61/707,625; and 61/590,259, which are hereby incorporated herein by reference in their entirety. Additionally, it is contemplated that the present disclosure can include a bezel such as that described in U.S. Pat. Nos. 8,827,517; 8,210,695; and 8,201,800, which are hereby incorporated herein by reference in their entirety.

It will be appreciated that embodiments of the invention described herein may be comprised of one or more conventional processors and unique stored program instructions that control one or more processors to implement, in conjunction with certain non-processor circuits, some, most, or all of the functions of the interior rearview mirror assembly 12, as described herein. The non-processor circuits may include, but are not limited to signal drivers, clock circuits, power source circuits, and/or user input devices. As such, these functions may be interpreted as steps of a method used in using or constructing a classification system. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used. Thus, the methods and means for these functions have been described herein. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation.

It will be understood by one having ordinary skill in the art that construction of the described invention and other components is not limited to any specific material. Other exemplary embodiments of the invention disclosed herein may be formed from a wide variety of materials, unless described otherwise herein.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It is also important to note that the construction and arrangement of the elements of the invention as shown in the exemplary embodiments is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present invention. The exemplary structures and processes disclosed herein are for illustrative purposes and are not to be construed as limiting.

It is also to be understood that variations and modifications can be made on the aforementioned structures and methods without departing from the concepts of the present invention, and further it is to be understood that such concepts are intended to be covered by the following claims unless these claims by their language expressly state otherwise.

What is claimed is:

1. An imaging system comprising:
a first light source configured to project a first illumination onto a vehicle occupant;
a second light source configured to project a second illumination onto the vehicle occupant; and
an imager configured to:
acquire one or more images of a biometric feature of the vehicle occupant;
generate image data corresponding to the one or more acquired images; and
automatically adjust a field of view based on the activation of a respective one of a plurality of light sources, a first field of view associated with activation of the first light source and a second field of view associated with activation of the second light source.

2. The imaging system as claimed in claim 1, wherein the first and second illuminations comprise light in a near infrared spectrum; and
wherein the second illumination has a longer wavelength than the first illumination.

3. The imaging system as claimed in claim 1, wherein the first illumination has a wavelength of one of 810 nm, 860 nm, and 880 nm; and
wherein the second illumination has a wavelength of 940 nm.

4. The imaging system as claimed in claim 1, wherein the imager is operable with a first field of view when only the first light source is activated and a second field of view when only the second light source is activated; and
wherein the second field of view is wider than the first field of view.

5. The imaging system as claimed in claim 4, wherein the first field of view has a first horizontal field component of approximately 20 degrees; and
wherein the second field of view has a second horizontal field component of approximately 60 degrees.

6. The imaging system as claimed in claim 1, wherein if only the first light source is activated, the biometric feature comprises an iris of the vehicle occupant and
wherein, if only the second light source is activated, the biometric feature comprises at least one of a face and a body of the vehicle occupant.

7. The imaging system as claimed in claim 1, wherein the imager comprises an image sensor with one of a red clear clear clear color filter array or no color filter array.

8. The imaging system as claimed in claim 1, wherein the imager comprises a zoom lens in optical communication with an image sensor; and
wherein the zoom lens is one of a variable zoom lens and a fixed zoom lens.

9. An imaging system comprising:
a first light source configured to project a first illumination onto a vehicle occupant;
a second light source configured to project a second illumination onto the vehicle occupant;

an imager having a variable field of view and configured to acquire one or more images of a biometric feature of the vehicle occupant and generate image data corresponding to the one or more acquired images; and a controller configured to:

automatically adjust a field of view based on whether the first or second illumination is being projected;

execute a first identification function by activating only the first light source and processing image data generated by the imager while operating with a first field of view; and execute a second identification function by activating only the second light source and processing image data generated by the imager while operating with a second field of view.

10. The imaging system as claimed in claim 9, wherein the first and second illuminations comprise light in a near infrared spectrum; and wherein the second illumination has a longer wavelength than the first illumination.

11. The imaging system as claimed in claim 9, wherein the first field of view comprises a first horizontal field component; and wherein the second field of view comprises a second horizontal field component that is wider than the first horizontal field component.

12. The imaging system as claimed in claim 9, wherein the first identification function comprises an iris scanning function to identify the vehicle occupant; and wherein the biometric feature comprises an iris of the vehicle occupant.

13. The imaging system as claimed in claim 9, wherein the second identification function comprises a driver monitoring function; and wherein the biometric feature comprises at least one of a face and a body of the vehicle occupant.

14. The imaging system as claimed in claim 9, further comprising an electrochromic mirror element;

wherein the controller selectively projects the first and second illuminations through the electrochromic mirror element; and wherein the imager is configured to acquire the one or more images through the electrochromic mirror element.

15. An imaging method comprising the steps of:

projecting a first illumination from a first light source or a second illumination from a second light source onto a vehicle occupant;

providing an imager having a variable field of view based on which of the first and second illumination is being projected;

using the imager to acquire one or more images of a biometric feature of the vehicle occupant;

generating image data corresponding to the one or more acquired images;

automatically adjusting a field of view based on whether the first or second illumination is being projected;

identifying the vehicle occupant by projecting only the first illumination and processing image data generated while the imager is operating with a narrow field of view; and monitoring the vehicle occupant by projecting only the second illumination and processing image data generated while the imager is operating with a wide field of view.

16. The imaging method as claimed in claim 15, wherein the first and second illuminations comprise light in a near infrared spectrum and wherein the second illumination has a longer wavelength than the first illumination.

17. The imaging method as claimed in claim 15, wherein the first illumination has a wavelength of one of 810 nm, 860 nm, and 880 nm; and wherein the second illumination has a wavelength of 940 nm.

18. The imaging method as claimed in claim 15, wherein the narrow field of view comprises a first horizontal field component of approximately 20 degrees; and wherein the wide field of view comprises a second horizontal field component of approximately 60 degrees.

19. The imaging method as claimed in claim 15, wherein the first and second illuminations are selectively projected through an electrochromic mirror element; and wherein the imager is configured to acquire the one or more images through the electrochromic mirror element.

* * * * *